(12) United States Patent
Gelbart et al.

(10) Patent No.: US 8,979,776 B2
(45) Date of Patent: Mar. 17, 2015

(54) LITHOTRIPSY SYSTEM WITH AUTOMATIC 3D TRACKING

(76) Inventors: Daniel Gelbart, Vancouver (CA); Lindsay Machan, Vancouver (CA)

( * ) Notice: Subject to any disclaimer, the term of this patent is extended or adjusted under 35 U.S.C. 154(b) by 1345 days.

(21) Appl. No.: 12/289,717

(22) Filed: Nov. 3, 2008

(65) Prior Publication Data
US 2009/0275866 A1 Nov. 5, 2009

Related U.S. Application Data

(63) Continuation-in-part of application No. 12/149,473, filed on May 2, 2008, now abandoned.

(51) Int. Cl.
*A61H 1/00* (2006.01)
*A61B 17/225* (2006.01)
*A61B 17/22* (2006.01)

(52) U.S. Cl.
CPC ............ *A61B 17/225* (2013.01); *A61B 17/2251* (2013.01); *A61B 17/2256* (2013.01); *A61B 2017/22028* (2013.01)
USPC ......... 601/4; 601/2; 601/1; 600/439; 600/437; 606/128

(58) Field of Classification Search
None
See application file for complete search history.

(56) References Cited

U.S. PATENT DOCUMENTS

| | | | | |
|---|---|---|---|---|
| 4,741,008 A * | 4/1988 | Franke | | 378/53 |
| 4,836,191 A * | 6/1989 | Noske et al. | | 601/4 |
| 4,844,079 A * | 7/1989 | Naser et al. | | 600/439 |
| 4,890,603 A * | 1/1990 | Filler | | 601/4 |
| 4,905,671 A * | 3/1990 | Senge et al. | | 601/4 |
| 4,913,156 A * | 4/1990 | Inbar et al. | | 600/439 |
| 4,915,114 A * | 4/1990 | Hassler | | 600/439 |
| 4,928,672 A * | 5/1990 | Grasser et al. | | 601/4 |
| 4,940,050 A * | 7/1990 | Forssmann et al. | | 601/4 |
| 4,945,898 A * | 8/1990 | Pell et al. | | 601/4 |
| 4,955,385 A * | 9/1990 | Kvalo et al. | | 600/439 |
| 4,960,108 A * | 10/1990 | Reichel et al. | | 606/2.5 |
| 4,971,039 A * | 11/1990 | Noske et al. | | 601/4 |
| 4,984,565 A * | 1/1991 | Rattner et al. | | 601/4 |
| 5,031,626 A * | 7/1991 | Hassler et al. | | 600/439 |
| 5,033,456 A * | 7/1991 | Pell et al. | | 601/4 |
| 5,065,761 A * | 11/1991 | Pell | | 600/439 |
| 5,070,861 A * | 12/1991 | Einars et al. | | 601/4 |
| 5,072,721 A * | 12/1991 | Weiler et al. | | 601/4 |
| 5,072,723 A * | 12/1991 | Viebach | | 601/4 |
| 5,078,124 A * | 1/1992 | Viebach et al. | | 601/4 |
| 5,131,392 A * | 7/1992 | Jolesz et al. | | 600/410 |
| 5,134,988 A * | 8/1992 | Pell et al. | | 601/4 |
| 5,137,014 A * | 8/1992 | Boehm | | 601/4 |
| 5,152,289 A * | 10/1992 | Viebach et al. | | 600/439 |

(Continued)

OTHER PUBLICATIONS

"Self Focusing on Extended Objects With Time Reversal Mirror—Applications to Lithotripsy" Jean Louis Thomas et al IEEE 1994 Ultrasonics Symposium pp. 1809-1814.

*Primary Examiner* — Nicholas Evoy
(74) *Attorney, Agent, or Firm* — Oyen Wiggs Green & Mutala LLP (57) ABSTRACT

A lithotripsy system capable of 3D tracking monitors the acoustic reflection from the stone in order to focus the shock wave on the stone regardless of shock wave displacement or stone movement. The tracking and focusing is based on a phased array concept, allowing the lithotripsy head to remain stationary and well coupled to the body. An alternate shock wave steering is based on refraction by a variable liquid wedge.

18 Claims, 8 Drawing Sheets

(56) References Cited

U.S. PATENT DOCUMENTS

| | | | |
|---|---|---|---|
| 5,152,767 A * | 10/1992 | Sypal et al. | 606/128 |
| 5,158,072 A * | 10/1992 | Wess et al. | 601/4 |
| 5,158,085 A * | 10/1992 | Belikan et al. | 600/439 |
| 5,178,136 A * | 1/1993 | Wess et al. | 601/4 |
| 5,181,512 A * | 1/1993 | Viebach et al. | 600/439 |
| 5,203,334 A * | 4/1993 | Brisson et al. | 600/439 |
| 5,209,222 A * | 5/1993 | Viebach et al. | 601/4 |
| 5,228,447 A * | 7/1993 | Harder et al. | 600/439 |
| 5,240,002 A * | 8/1993 | Brisson et al. | 600/439 |
| 5,245,988 A * | 9/1993 | Einars et al. | 601/4 |
| 5,251,614 A * | 10/1993 | Cathignol et al. | 601/4 |
| 5,263,076 A * | 11/1993 | Elff et al. | 378/162 |
| 5,301,659 A * | 4/1994 | Brisson et al. | 601/4 |
| 5,329,928 A * | 7/1994 | Brisson et al. | 600/439 |
| 5,399,146 A * | 3/1995 | Nowacki et al. | 601/4 |
| 5,409,002 A * | 4/1995 | Pell | 600/407 |
| 5,658,239 A * | 8/1997 | Delmenico | 601/4 |
| 5,770,801 A * | 6/1998 | Wang et al. | 73/644 |
| 5,836,898 A * | 11/1998 | Schwieker | 601/4 |
| 6,093,148 A | 7/2000 | Fujimoto | |
| 6,719,449 B1 * | 4/2004 | Laugharn et al. | 366/127 |
| 6,869,407 B2 * | 3/2005 | Ein-Gal | 601/2 |
| 6,942,617 B2 | 9/2005 | Liang et al. | |
| 6,948,843 B2 * | 9/2005 | Laugharn et al. | 366/127 |
| 7,048,699 B2 * | 5/2006 | Ein-Gal | 601/2 |
| 7,329,039 B2 * | 2/2008 | Laugharn et al. | 366/114 |
| 7,438,695 B2 * | 10/2008 | Buchholtz et al. | 601/4 |
| 7,493,155 B2 * | 2/2009 | Kaltschmidt et al. | 600/427 |
| 7,517,328 B2 * | 4/2009 | Hoffmann | 601/46 |
| 7,785,276 B2 * | 8/2010 | Bohris | 601/2 |
| 8,298,162 B2 * | 10/2012 | Del Giglio | 601/2 |
| 2002/0009015 A1 * | 1/2002 | Laugharn et al. | 366/108 |
| 2003/0050559 A1 * | 3/2003 | Ein-Gal | 600/437 |
| 2003/0060738 A1 * | 3/2003 | Ein-gal | 601/4 |
| 2004/0264293 A1 * | 12/2004 | Laugharn et al. | 366/127 |
| 2005/0015023 A1 * | 1/2005 | Ein-Gal | 601/2 |
| 2005/0038361 A1 * | 2/2005 | Zhong et al. | 601/4 |
| 2005/0150830 A1 * | 7/2005 | Laugharn et al. | 210/634 |
| 2006/0029525 A1 * | 2/2006 | Laugharn et al. | 422/130 |
| 2006/0158956 A1 * | 7/2006 | Laugharn et al. | 366/127 |
| 2007/0065420 A1 * | 3/2007 | Johnson | 424/93.7 |
| 2007/0239074 A1 * | 10/2007 | Ein-Gal | 601/2 |
| 2008/0009885 A1 * | 1/2008 | Del Giglio | 606/128 |
| 2008/0050289 A1 * | 2/2008 | Laugharn et al. | 422/128 |
| 2008/0319356 A1 * | 12/2008 | Cain et al. | 601/2 |
| 2009/0275832 A1 * | 11/2009 | Gelbart et al. | 600/439 |
| 2009/0275866 A1 * | 11/2009 | Gelbart et al. | 601/4 |
| 2011/0054363 A1 * | 3/2011 | Cain et al. | 601/4 |
| 2011/0257523 A1 * | 10/2011 | Hastings et al. | 600/439 |
| 2011/0257561 A1 * | 10/2011 | Gertner et al. | 601/2 |
| 2011/0263967 A1 * | 10/2011 | Bailey et al. | 600/411 |
| 2012/0065492 A1 * | 3/2012 | Gertner et al. | 600/411 |
| 2012/0065493 A1 * | 3/2012 | Gertner | 600/411 |
| 2012/0065494 A1 * | 3/2012 | Gertner et al. | 600/411 |
| 2012/0109018 A1 * | 5/2012 | Gertner et al. | 601/2 |
| 2013/0018287 A1 * | 1/2013 | Capelli | 601/2 |
| 2013/0211294 A1 * | 8/2013 | Bohris | 601/4 |

\* cited by examiner

LITHOTRIPSY SYSTEM WITH AUTOMATIC 3D TRACKING

This application is a continuation-in-part of U.S. application Ser. No. 12/149,473 filed 2 May 2008 and entitled LITHOTRIPSY SYSTEM WITH AUTOMATIC 3D TRACKING.

FIELD OF THE INVENTION

The invention is in the medical field and is particularly useful for breaking up kidney stones, a process known as Lithotripsy or Extracorporeal Shock Wave Lithotripsy (ESWL).

BACKGROUND OF THE INVENTION

Figure 1:
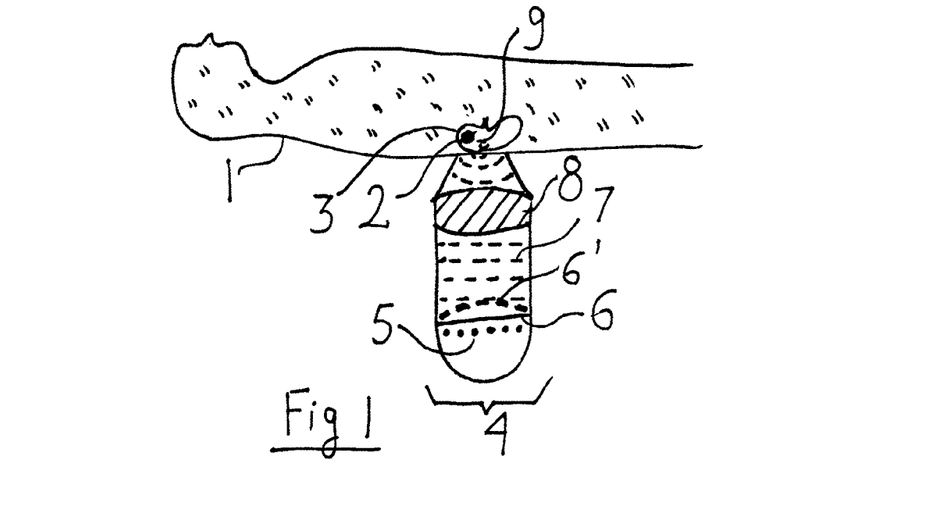
FIG. 1 is a longitudinal section of prior at lithotripsy systems.
Figure 2:
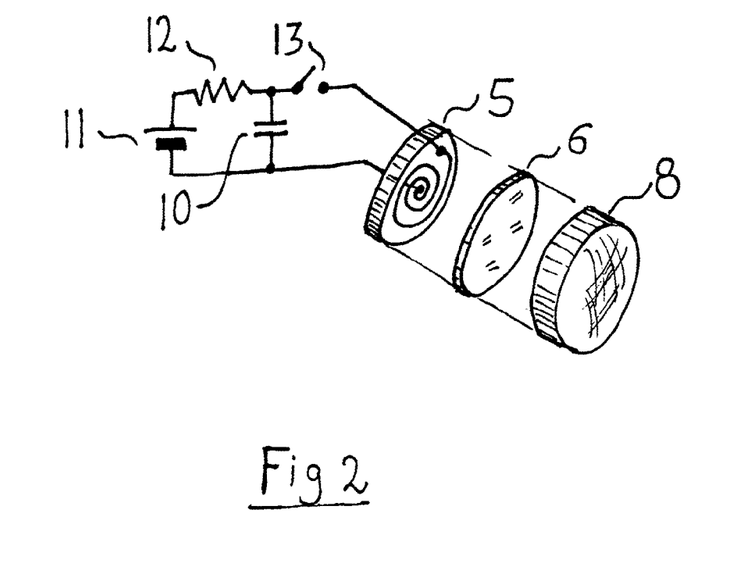
FIG. 2 is an "exploded" view of a prior art lithotripsy head.

The Lithotripsy process is used for breaking up kidney stones and other stones formed in the body without the need for surgery. Once stone are broken up into small fragments they can leave the body through the renal system. The stones are broken up by focusing an acoustic pulse or shockwave. Early systems used a spark gap as an acoustic energy source. Newer systems use the repulsion of a conductive diaphragm from an energized coil to generate a shock wave in a liquid, typically water, which is focused and coupled into the body. The prior art is shown in FIGS. 1 and 2. A major problem in prior art systems is a lack of an active mechanism to keep the shock wave focused on the stone. When shock wave is not focused on the stone damage to the kidney and other organs can occur. In order to minimize this damage current systems use power levels below optimal. Current systems also spread the size of the beam at the focal point to cover an area larger than the stone, in order not to miss the stone. This further reduces power density and increases tissue damage. At lower power density the stone does not disintegrate completely, causing extra difficulty in passing the fragments through the renal system. The reason the shock wave can not be precisely placed on the stone is the constant movement of the kidney, mainly because of breathing, as well as the fact that the shock waves are not visible to the x-ray or ultrasound equipment used to locate the stone, so the operator has to estimate where the point of maximum shock wave intensity, or focus, is located, without actually being able to see it. Since different tissues have different acoustic velocities the focal point inside the body may be different than the focal point measured in water during calibration. In general there are two types of errors: pointing errors (or x-y errors) and focusing errors (z axis errors). A three dimensional (3D) tracking system can eliminate or reduce x, y and z axis errors.

U.S. Pat. Nos. 4,913,156, 4,915114, 5,031,626, 5,158,085 and 6,942,617 offers a partial solution by mechanically moving the lithotripsy head in response to an ultrasound scanner continuously imaging the stone. Because of the large mass of the lithotripsy equipment the tracking rate possible by mechanical tracking is limited. Also, the main problem is not solved by this patent as the spatial position of the shock wave focus is assumed, not continuously measured and tracked. If there is any calibration error or a displacement caused by tissue, the system will track an imaginary focus which may be offset from the real focus of the shockwave. This risk prevents higher powers from being used, as in the case of an offset the shockwave will always focus on the tissue instead of the stone. A further limitation of any system requiring mechanical steering of the lithotripsy head is that any relative motion between the head and the body affects coupling efficiency and introduces further errors by deforming the tissue or the coupling fluid. By the way of example, when the tissue or coupling fluid inside lithotripsy head is deformed from a parallel shape to a wedge shape the direction of the beam will change. Any air gap introduced during such motion will prevent energy coupling to the tissue.

U.S. Pat. No. 5,658,239 uses the reflected shock wave to locate the stone but relies on mechanical motion of the whole lithotripsy head to correct for placement errors. As before, the large mass of the head prevents effective tracking and changes of the head to tissue interface are undesirable.

U.S. Pat. No. 5,131,392 uses a phased array inside an MRI machine to focus a shock wave, in conjunction with the capability of MRI to locate the stone. Again, the locating mechanism is separate from the shockwave mechanism, allowing an offset error to exist. Furthermore, in an MRI machine very poor acoustic coupling exists between the large spherical machine and the target tissue, not allowing the efficient and localized coupling of a lithotripsy system.

It is desired to have a compact 3D tracking system (tracking both pointing errors and focus errors) which continuously aligns the actual shock wave focus with the stone, regardless of shock wave displacements inside the body. Furthermore, it is desired to track without the use of moving parts, in order to achieve high tracking rate. It is also desired to track without introducing relative motion between the lithotripsy head and the body tissue. It is further desired to focus the shock wave to the smallest practical spot in order to achieve the highest degree of stone disintegration. These and other objects of the invention will become apparent from the drawings and the disclosure.

SUMMARY OF THE INVENTION

A lithotripsy system capable of 3D tracking monitors the acoustic reflection from the stone in order to focus the shock wave on the stone regardless of shock wave displacement or stone movement. The tracking and focusing is based on a phased array concept, allowing the lithotripsy head to remain stationary and well coupled to the body. An alternate shock wave steering is based on refraction by a variable liquid wedge.

DETAILED DESCRIPTION

A typical lithotripsy system is shown in FIG. 1. A patient 1 has a stone 2 (also known as calculus) inside kidney 3. A lithotripsy head 4 generates a focused shock wave 9 which disintegrates the stone 2. The shock wave is generated by an electromagnetic transducer comprising of coil 5 and diaphragm 6. When a very large current pulse is passed through coil 5 it repels diaphragm 6 (which acts as a short circuited secondary coil). Diaphragm 6 bends briefly into shape 6' and creates an acoustic shock wave in liquid 7, typically water. Lens 8 focuses shock wave 9 into a small area. Head 4 has to make intimate contact with body 1 at all times. Acoustic lens 8 operates similar to an optical lens and is made from a material having slower (for convex lens) or faster (for concave lens) acoustic velocity than water. Shock wave velocity in water is about 1500 m/s. For slower velocity polymers can be used, for higher velocity some polymers and most metals can be used. A more detailed view of the lithotripsy head is shown in FIG. 2. Coil 5 is usually a flat coil wound on a ceramic substrate. Diaphragm 6 is placed very close to the coil; it is shown here further away for clarity. To generate a large current pulse a capacitor 10 is charged from a power supply 11 and suddenly discharged by closing electronic switch 13. Typical discharge rate is 1-5 Hz. Switch 13 can be one of many well known solid state switching elements such as a MOSFET, SCR, IGBT bipolar transistor or other. The technology of lithotripsy machines is well known in the art and such machines are commercially available for over 25 years. More data can be found in websites of suppliers, such as Siemens Medical Systems (www.medical.siemens.com).

Figure 3:
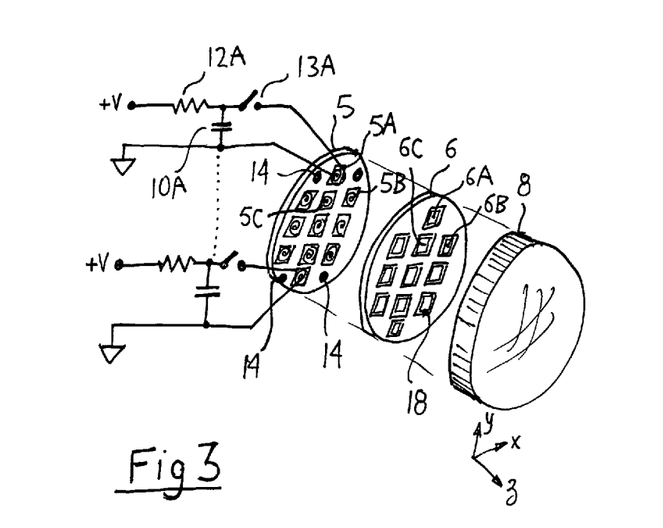
FIG. 3 is an "exploded" view of a lithotripsy head using an electromagnetic phased array.

In order to steer the shock wave focal point to coincide with the stone an electromagnetic phased array transducer is used, as shown in FIG. 3. This allows moving the focal point of the shockwave in three dimensions without moving the lithotripsy head. The coil 5 is divides into many segments marked 5A, 5B, 5C, etc. Each segment can be driven independently by switches 13A, 13B, 13C etc. discharging capacitors 10A, 10B, 10C, etc. Capacitors are recharged by resistors 12A, 12B, 12C etc. Diaphragm 6 is also divided into corresponding zones 6A, 6B, 6C etc. Each one of these zones is capable of moving a small amount without affecting adjacent zones. This can be achieved by adding flexibility to the diaphragm at the boundary of the zones. One method of adding flexibility is by embossed convolutions 18. When assembled, diaphragm 6 is in close proximity to coil 5, but need not be close to lens 6 as the gap between diaphragm 6 and lens 8, as well as the gap between lens 8 and the body of the patient is filled with an acoustic coupling fluid such as water. For lower acoustic reflection the surfaces of lens 8 can be coated with a different material having an acoustic velocity between that of the fluid and that of the lens material, similar to the well known principle of optical anti reflective coatings. It is well known that a phased array transducer can control the wavefront of the shock wave and such a control can be used to great advantage in at least three ways:

1. Steering the beam in any desired direction by tilting the wavefront.
2. Changing the focal point of the bean by changing wavefront curvature.
3. Compensation for aberrations in the transducer and in the acoustic path by using an arbitrary deformation of the wavefront.

In order to automatically track the stone it may be desired to detect the acoustic reflection of the stone. This can be done by incorporating piezoelectric sensors 14 in the transducer array.

Figure 4:
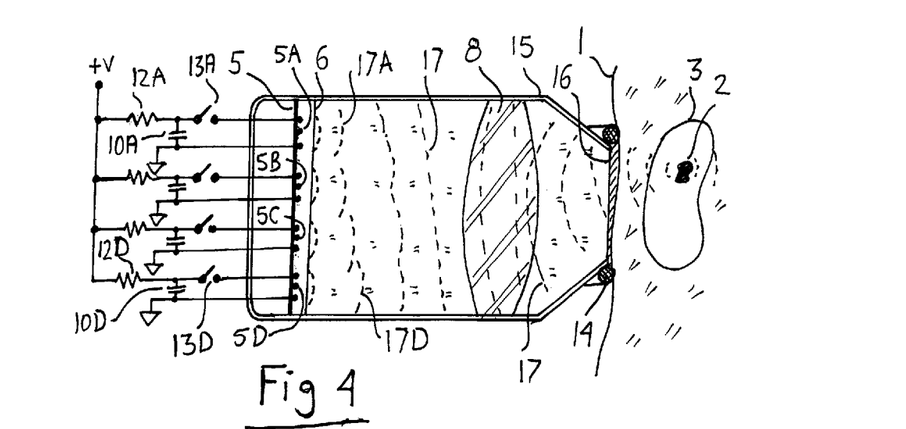
FIG. 4 is a longitudinal section of a lithotripsy head based on an electromagnetic phased array.
Figure 5:
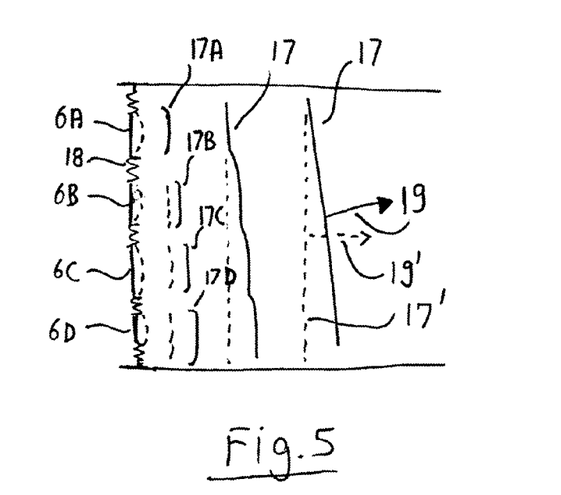
FIG. 5 is a schematic representation of shock wave steering using an electromagnetic phased array.
Figure 6:
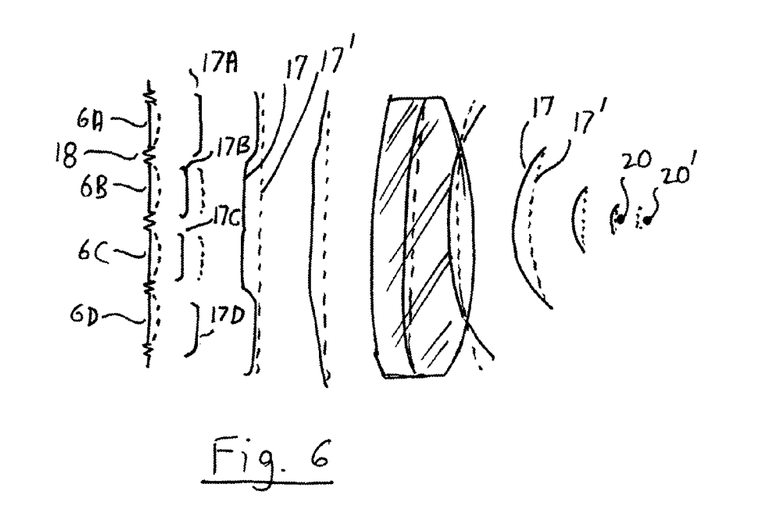
FIG. 6 is a schematic representation of shock wave focusing using an electromagnetic phased array.

The method of steering the shockwave is shown in FIG. 4. To move the direction of the shockwave, in order to hit stone 2, wavefront 17 needs to be tilted. To generate a tilted wavefront, coils 5A, 5B, 5C and 5D need to be energized with a small delay relative to each other, creating time delayed partial wavefronts 17A to 17D. These merge into a single tilted wavefront 17. The time delays are created by sequentially activating witches 13A to 13D. While the example only uses four segments to create a wavefront, clearly the division of coil 5 into smaller coils 5A, 5B etc. is a matter of choice. Dividing into more elements creates smoother wavefronts but reduces the overall efficiency and increases the complexity of the electronic system. A preferred array size is from 2×2 to 20×20 elements. It is also possible to use asymmetric resolution, for example by dividing a circle into 6×10 elements or using rectangular arrays. The advantage of asymmetric division is allowing to use different resolutions in x and y direction. For example, most stone movements are in a single direction because of breathing. The lithotripsy head is enclosed in housing 15 having a flexible front diaphragm 16 in order to allow intimate contact with the body (typically by using a coupling gel). As in all acoustic systems, it is desired to keep the acoustic impedance as uniform as possible to prevent reflections. In order to track stone 4 piezoelectric or other sensors can be used to detect the acoustic reflection. A possible location for acoustic sensors 14 is shown in FIG. 3. By the way of example, to tilt wavefront 17 by 10 degrees in a 20 cm diameter head, the tilt of the wavefront needs to be 20 tan $10°$=3.5 cm. Since the acoustic velocity is about 1500 m/s for water, coil 5A has to be delayed by 35/1500=0.023 mS or 23 uS relative to coil 5D. Coils 5B and 5C are delayed approximately 8 uS and 15 uS. FIG. 5 shows the generation of a tilted wavefront in a schematic way. The original wavefront 17', created by simultaneous movements of segments 6A to 6D, had a propagating direction 19'. The new wavefront 17 propagates in direction 19. Obviously both the lens 8 and housing 15 in FIG. 4 have to be sufficiently large to accommodate the tilted wavefront. FIG. 6 shows, in a schematic way, the generation of a curved wavefront to change the distance the beam comes to a focus. If the focal point needs to be moved from position 20' to position 20, which is closer, the wavefront 17 needs to be more concave than the original wavefront 17'. This is achieved by delaying the discharge pulse to the central transducers, causing diaphragm segments 6B and 6C to move later than 6A and 6D. At an acoustic velocity of 1500 m/s, every uS of delay bends the wavefront by about 1.5 mm.

Figure 7:
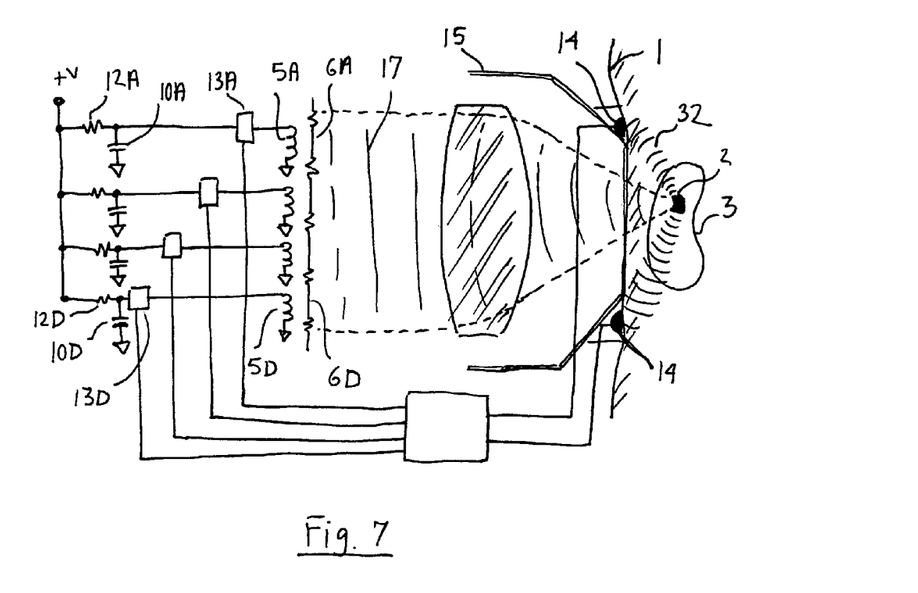
FIG. 7 is a schematic representation of the tracking control system.
Figure 8:
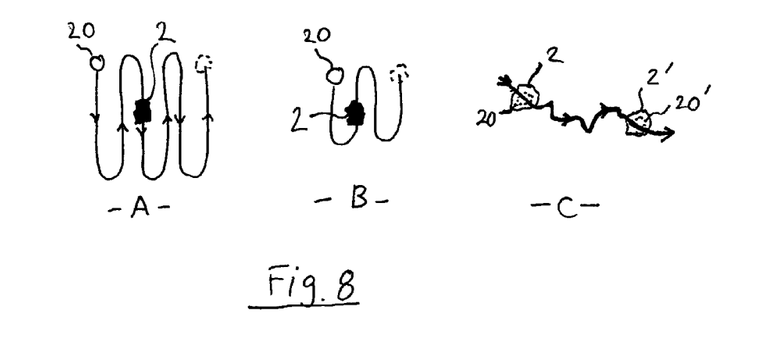
FIG. 8A shows the process of locating the stone by the initial scan of the shockwave focal point.
FIG. 8B shows the process of tracking the stone by a small area scan.
FIG. 8C shows the focal point trajectory in continuous tracking.

An example of an automatic tracking system is shown in FIG. 7. After each pulse the intensity of the reflected acoustic signal is detected by sensors 14. Typically 2 sensors are used for the x direction and 2 for the y direction. When shock wave is focused on stone 2 the intensity of the reflection is about equal in all directions. When one sensor receives a stronger signal than the others it indicates that the focal spot is drifting off and the wavefront needs to be tilted in order to re-center spot. Since the acoustic signal picked up by sensors 14 is also a function of distance (because of the divergence of the reflected wave 32), computer 21 needs to correct the signal intensity by the square of the distance. The distances are known by the arrival times of the reflections 32 compared to the time of the pulse. The computer 21 adjusts the wavefront 17 to keep the focused spot on the stone by changing the delay times of switches 13A-13D. Because of the uncertainty in the shape of the stone, causing an uncertainty in the intensity of the reflected waves, a different control system can be used. It is based on locating the stone by scanning rather than continuous tracking. In this mode no distance correction for the sensors is required and it is not sensitive to the shape of the stone. The system only looks at the sum of the signals from the sensors. In this mode the focal spot 20 is scanned over the area the stone 2 is expected to be in, as shown in FIG. 8A. The scanning is done at a reduced power, to avoid tissue damage, and at a much higher pulsing frequency, in order to speed the process up. When the scanned bean passes over the stone an increased reflection is sensed in sensors 14. This position is noted (by storing the time delays generating the corresponding wavefront tilts) and used to generate the full power pulse. For subsequent pulses a reduced scanning area can be used, since the stone movement is small between pulses. This limited scan is shown in FIG. 8B. The spot trajectory in a continuous tracking mode is shown in FIG. 8C. FIG. 8C shows the stone moving from position 2 to position 2' and the spot 20 tracking it from position 20 to position 20'. After the stone was located by using the above methods of scanning or continuous tracking, a separate scan can be performed in the z, or focus, direction. The best focus will generate the largest total reflection (i.e. sum of detectors 14). This wavefront curvature is noted (again by storing the time delays used to generate it) and used for the full power pulse. Continuous 3D scanning or tracking is also possible. More elaborate wavefront shaping algorithms can be used for aberration correction, shaping size of focal spot to match stone and other advantages. Such algorithms are well known in the art of phased array transducers used in ultrasonics and optics.

Besides the tracking and scanning modes a more conventional stone location method, such as ultrasound or x-ray, can be used in conjunction with the phased array wavefront steering. The imaging device determines the stone location and the time delays are automatically set to point the shockwave to that location. In this mode an offset can exist between the assumed focus location and the actual focus location, but it still has an advantage over prior art because shockwave is steered without moving lithotripsy head, allowing fast steering.

Figure 9:
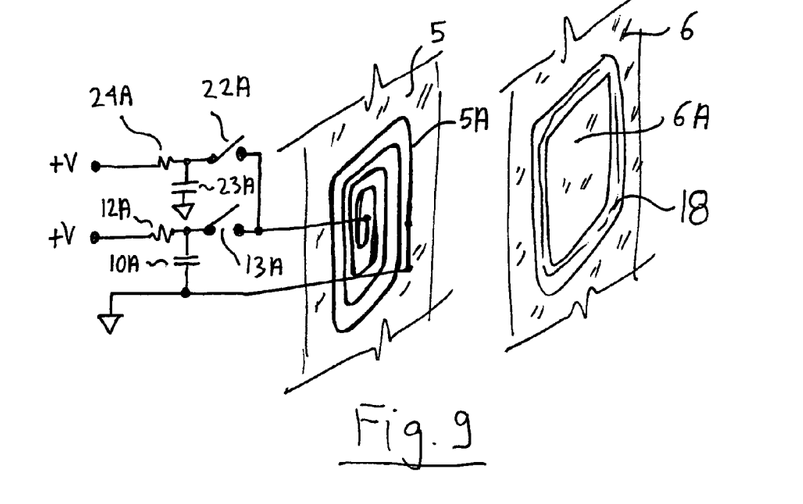
FIG. 9 is a schematic representation of supplying two power levels to the electromechanical transducer.

FIG. 9 shows a method of generating two pulse intensities. Discharging capacitor 10A via switch 13A generates a large shockwave pulse at a typical rate of 1-5 Hz. Discharging much smaller capacitor 23A via switch 22A generates the weaker scanning pulse. Since capacitor 23A is much smaller it recharges much faster, allowing a pulsing rate of 10 Hz-1 KHz during scanning to speed up scanning.

Figure 10:
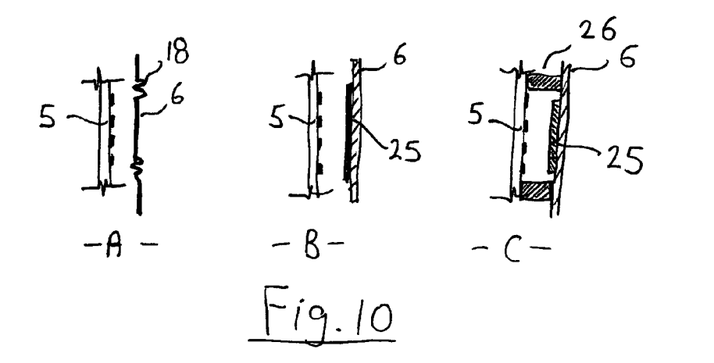
FIG. 10A is a section of the electromechanical transducer using a metallic diaphragm.
FIG. 10B is a section of the electromechanical transducer using a polymeric diaphragm with metallic inserts.
FIG. 10C is a section of the electromechanical transducer using a metallic or polymeric diaphragm with separating walls between transducers.
Figure 11:
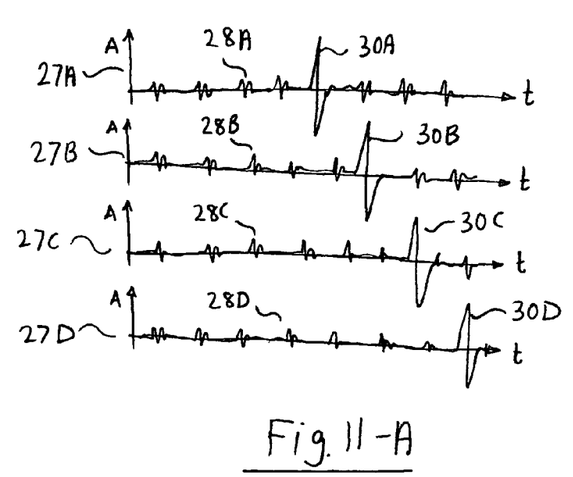
FIG. 11A shows the amplitude of the shockwaves as a function of time when using pulsed tracking.
FIG. 11B shows the amplitude of the shockwaves as a function of time when using continuous wave tracking.

FIG. 10 depicts different constructions of the electromagnetic transducer cells. In FIG. 10A a flat coil 5 is placed adjacent to a metal diaphragm 6 with embossed convolutions 18 for increases flexibility. In FIG. 10B diaphragm 6 is made of a flexible polymer such as silicone rubber or polyurethane with thin metal plates 25 bonded to it in order to be repelled by coil 5. In FIG. 10C rigid partitions 26 were added between transducer cells in order to minimize mechanical coupling. FIGS. 11A and 11B show typical acoustic waveforms generated by the lithotripsy head. The waveforms of four transducers are shown as graphs 27A to 27D as a function of time. In FIG. 11A the low energy pulses 28A-28D are used for scanning (by changing pulse delays) and the large pulses 30A-30D are used to disintegrate the stone, once stone is located or tracked by the lower energy pulses. The scanning or tracking can also be done by using a continuous wave (CW) for scanning or tracking. This is shown in FIG. 11B. The wavefront is changed by changing the phase of the CW inputs to the transducers, creating phase shifted pressure waves 31A-31D.

While this disclosure emphasized kidney stones it should be understood that the term Lithotripsy in this disclosure applies to any system used to couple acoustic energy to other items in the body such as gall bladder stones, tumors etc. In such cases the end result is the destruction of the undesired object in the target area, not necessarily by disintegration. Is some cases the destruction is achieved by heating, cavitation, cell damage or other means. While the preferred embodiment uses a electrodynamic phased array, based on coils and metallic diaphragms, other phased arrays can be used such as piezoelectric or magnetostrictive. Magnetostrictive arrays can be based on Terfenol-D, a material with a very large magnetostrictive coefficient. By the way of example, an array based on 100 mm long Terfenol-D rods will create 0.1 movement at a magnetic field of under 2 Tesla.

In some applications it may be desired to use a continuous acoustic wave (CW) for the destruction of the target instead of shockwave pulses. This is beneficial in application which are based on heating the object, such as destruction of tumors. The disclosure should be broadly interpreted to cover all modes of pulsed and continuous energy: pulsed tracking and pulsed destruction, CW tracking and CW destruction, CW tracking and pulsed destruction as well as pulsed tracking and CW destruction. Also the term "tracking" should be interpreted in the broadest sense to mean all methods of keeping the focus of the shockwave places on the target. This comprises continuous tracking, dithering, sampling, scanning to find the target and any other methods known from control theory to keep a beam on a target.

Figure 12:
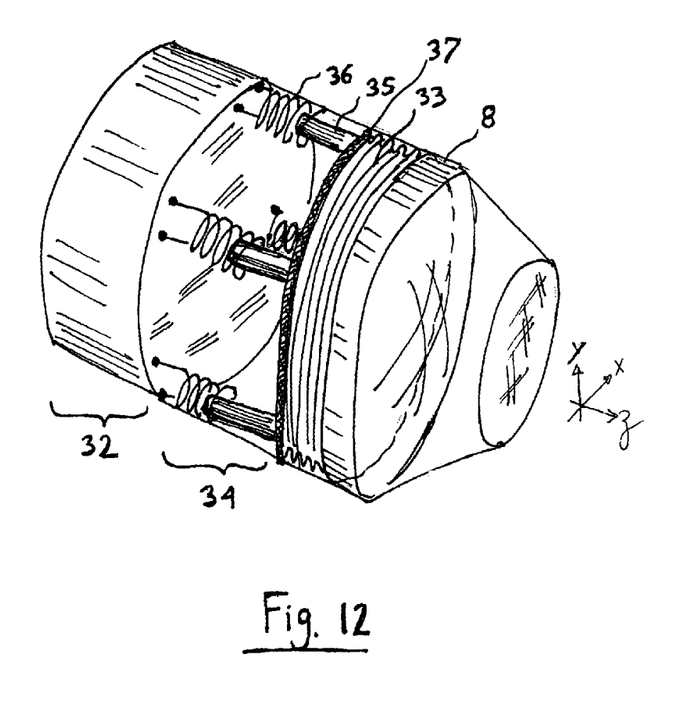
FIG. 12 is an isometric view of a lithotripsy head based on liquid wedge steering.

An alternative method of acoustic shock wave steering is shown in FIG. 12. In this method the lithotripsy system part in contact with the body of the patient contains a steering device capable of steering the shock wave without moving the part in contact with the body. For example, the shock wave is steered by refraction. The shock wave is generated by a conventional lithotripsy generator (not a phased array) 32 and passes through a deformable liquid cell. The liquid in this cell is separated from the liquid filling the lithotripsy head by bellows 33 and plate 37. Lens 8 forms a seal on the other side of the bellows. By tilting plate 37 using actuators 34 a liquid wedge, or prism, is formed which steers the shockwave. The actuators can be of the moving coil or moving magnet type as well as any other type of actuator such as fluidic actuators. They require a bandwidth of about 10 Hz to track the movement of the stone. By example, four permanent magnets 34 can be mounted on plate 37 and four coils 36 can be mounted on the lithotripsy head. The actuator pair controlling each axis are wired for a push-pull operation, this when one actuator is pushing the other is pulling causing plate to tilt. Since there is a separate pair for the other axis, the plate can tilt in two axes simultaneously, providing x-y steering. Focal adjustment is also possible by adding a fifth actuator (not shown) changing the curvature of plate 37.

Figure 13:
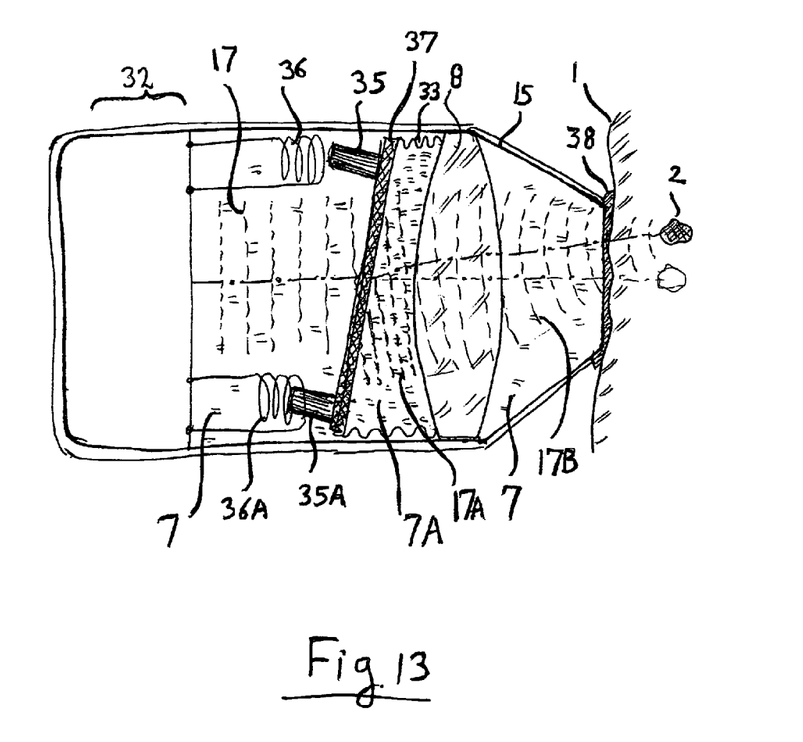
FIG. 13 is a section of a lithotripsy head based on liquid wedge steering.

FIG. 13 shows the operation of the shockwave steering. Conventional lithotripsy generator 32 generates a parallel wavefront 17 focused by lens 8. Energizing coils 36 and 36A tilts plate 37 to form a liquid wedge. Liquid 7A has a different acoustic velocity from liquid 7 and lens 8. In the example of FIG. 7 the acoustic velocity of liquid 7A is higher, causing the wavefront 17A to tilt upwards, and after being focused by lens 8 it hits stone 2 at a higher position. The effect is similar to bending light by an optical prism, and it obeys Snell's law. All other details of operation are similar to the ones discussed previously, such as the stone tracking system. The main difference that the shock wave steering mechanism has moving parts, however the lithotripsy head does not move relative to the patient 1 and coupling efficiency is maintained via gel 38. In order to minimize reflections the acoustic velocity of the material used for plate 37 should be the geometric mean of the velocities in liquids 7 and 7A. The larger the difference in acoustic velocities between liquids 7 and 7A, the lower the tilt angle has to be (by about the same ratio) and the faster the system can track.

By the way of example, if liquid 7 is water (v=1480 m/s) liquid 7A can be glycerine (v=1904 m/s). Plate 37 can be neoprene (v=1600 m/s) as $1600 \sim (1480 \times 1904)^{0.5}$. These materials are also chemically compatible, and neoprene is a flexible material so focusing can be achieved by changing the curvature of plate 37.

A higher performance system uses carbon tetrachloride (v=926 m/s) or ether (v=985 m/s) for liquid 7A and glycerine for liquid 7, with plate 37 made of PTFE (Teflon). The acoustic velocity in Teflon is 1350 m/s, which are an almost exact match for these liquids, as $(926 \times 1904)^{0.5}=1328$ m/s and $(985 \times 1904)^{0.5}=1369$ m/s. PTFE is also compatible with those liquids and is flexible. Since the difference in velocity between the liquids is very large, small plate deflections cause large steering. For example, when plate 37 is tilted by 1 degree the wavefront is tilted by $1 \deg \times 1904/926 = 2.06$ degrees. For a system with a focal length of 20 cm the focal point will move about 6 mm.

A less desired implementation uses a conventional lithotripsy head coupled to the patient's body with a bellows. The head can be tilted for shock wave steering without tilting the part in contact with the body. This implementation is less desirable as the moving mass is large.

The invention claimed is:

1. A lithotripsy system for the tracking and the destruction of a moving object inside the body of a patient, the system comprising:
   a lithotripsy head comprising at least one transducer operable to generate shockwaves focused on said moving object, a shockwave steering device and a body-contacting portion wherein the body-contacting portion is configured to contact the body of the patient and to transmit the shockwaves into the body of the patient;
   a tracking system configured to track the moving object in at least two dimensions, the tracking system comprising a plurality of acoustic detectors configured to sense acoustic reflections from said moving object, and
   said shockwave steering device configured to variably tilt wavefronts of the shockwaves in response to tracking information from the tracking system to keep said shockwaves focused on said moving object, said shockwave steering device operable to tilt the wavefronts while the body-contacting portion of the lithotripsy head and the at least one transducer remain fixed relative to the body of said patient, and wherein the shockwave steering device comprises a liquid wedge;
   an acoustic lens located to focus the wavefronts of the shockwaves that have been tilted by the shockwave steering device whereby the tilting of the wavefronts by the shockwave steering device causes a corresponding displacement in a location at which the wavefronts of the shockwaves are focused by the acoustic lens; and,
   wherein the liquid wedge comprises a plate having a first fluid on one side of the plate and a second fluid on a second side of the plate wherein the speed of sound is different in the first and second fluids and the shockwave steering device comprises a first actuator for tilting the plate.

2. A lithotripsy system according to claim 1 further comprising a source of a pulsed acoustic wave wherein said acoustic reflections comprise reflections of the pulsed acoustic wave.

3. A lithotripsy system according to claim 1 further comprising a source of a continuous acoustic wave wherein said acoustic reflections comprise reflections of the continuous acoustic wave.

4. A lithotripsy system according to claim 1 wherein the at least one transducer is operable for generating low power acoustic waves for generating said acoustic reflections from the object.

5. A lithotripsy system according to claim 4 wherein said low power acoustic waves comprise pulsed acoustic waves.

6. A lithotripsy system according to claim 4 wherein said low power acoustic waves comprise continuous acoustic waves.

7. A lithotripsy system according to claim 4 wherein said system for generating a shockwave is also operable to generate low power acoustic waves for generating the said acoustic reflections from the object.

8. A lithotripsy system according to claim 1 wherein said liquid wedge is electromagnetically actuated.

9. A lithotripsy system according to claim 1 wherein said liquid wedge comprises a layer of glycerine.

10. A lithotripsy system according to claim 1 wherein said acoustic lens is coated with an anti-reflection acoustic coating.

11. A lithotripsy system according to claim 1 wherein the shockwave steering device further comprises a second actuator for altering a curvature of the plate.

12. A lithotripsy system according to claim 11 wherein the first fluid comprises glycerine.

13. A lithotripsy system according to claim 12 wherein the second fluid comprises water.

14. A lithotripsy system according to claim 1 wherein the second fluid is in a chamber filling a space between the plate and an acoustic lens.

15. A lithotripsy system according to claim 1 wherein the first actuator for tilting the plate comprises a plurality of electromagnetic actuators connected between the plate and the lithotripsy head.

16. A lithotripsy system for the tracking and the destruction of a moving object inside the body of a patient, the system comprising:
   a lithotripsy head comprising at least one transducer operable to generate shockwaves focused on said moving object, a shockwave steering device and a body-contacting portion wherein the body-contacting portion is configured to contact the body of the patient and to transmit the shockwaves into the body of the patient;
   a tracking system configured to track the moving object in at least two dimensions, the tracking system comprising a plurality of acoustic detectors configured to sense acoustic reflections from said moving object;
   said shockwave steering device configured to variably tilt wavefronts of the shockwaves in response to tracking information from the tracking system to keep said shockwaves focused on said moving object, said shockwave steering device operable to tilt the wavefronts while the body-contacting portion of the lithotripsy head and the at least one transducer remain fixed relative to the body of said patient;

wherein the at least one transducer comprises a phased array of transducers and the shockwave steering device comprises a controller configured to energize the transducers of the phased array in a time sequence to tilt the wavefronts of the shockwaves; and, wherein the phased array of transducers comprises a diaphragm divided into an array of independently-deflectable zones and at least one electromagnetic actuator coupled to the diaphragm to drive motion of the diaphragm in each of the zones.

17. A lithotripsy system according to claim 16 wherein the at least one electromagnetic actuator each comprises a capacitor, and a switch controlling discharge of the capacitor into a coil.

18. A lithotripsy system according to claim 16 wherein the tracking system comprises piezoelectric sensors incorporated into the phased array of transducers.

* * * * *